United States Patent [19]

Naylor et al.

[11] Patent Number: 4,877,794
[45] Date of Patent: Oct. 31, 1989

[54] 2-ALKOXY-N-(1-AZABICYCLO(2.2.2)OCT-3-YL) BENZAMIDE AND THIOBENZAMIDE COMPOSITIONS AND THE USE THEREOF TO TREAT SCHIZOPHRENIA

[75] Inventors: Robert J. Naylor; Brenda Naylor, both of Ilkley, England

[73] Assignee: A. H. Robins Company, Incorporated, Richmond, Va.

[21] Appl. No.: 240,868

[22] Filed: Sep. 6, 1988

[30] Foreign Application Priority Data

Sep. 4, 1987 [GB] United Kingdom ............... 8720805

[51] Int. Cl.⁴ .......................................... A61U 31/44
[52] U.S. Cl. ................................................. 514/305
[58] Field of Search ........................................ 514/305

[56] References Cited

U.S. PATENT DOCUMENTS 4,093,734  6/1978  Kruger et al. ...................... 424/274
4,593,034  6/1986  Munson, Jr. et al. ............... 424/274

FOREIGN PATENT DOCUMENTS 0099789  2/1984  European Pat. Off.
0158532  10/1985  European Pat. Off.
0201165  11/1986  European Pat. Off.
0202062  11/1986  European Pat. Off.
2125398  3/1984  United Kingdom.

OTHER PUBLICATIONS

Mikhlina et al., *Chem. Abstr.* 65:2220b (1966).
Mikhlina et al., *Chem. Abstr.* 79:146358a (1973).
Mikhlina et al., *Chem. Abstr.* 86:155489r (1977).
Krueger, G. et al., *Chem. Abstr.* 87:68001(c) (1977).

*Primary Examiner*—Stanley J. Friedman
*Attorney, Agent, or Firm*—Saidman, Sterne, Kessler & Goldstein

[57] ABSTRACT

2-Alkoxy-N-(1-azabicyclo[2.2.2]oct-3-yl) benzamides and thiobenzamides having the formula

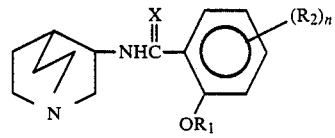

wherein X is oxygen or sulphur; $R_1$ is loweralkyl; and $R_2$ is hydrogen, halo, 4,5-benzo, alkoxy or Am wherein Am is amino, methylamino or dimethylamino, and n is 1 or 2, and the pharmaceutically acceptable acid addition salts thereof have antischizophrenic activity.

8 Claims, 3 Drawing Sheets

2-ALKOXY-N-(1-AZABICYCLO(2.2.2)OCT-3-YL) BENZAMIDE AND THIOBENZAMIDE COMPOSITIONS AND THE USE THEREOF TO TREAT SCHIZOPHRENIA

FIELD OF THE INVENTION

The present invention relates to the use of certain N-(3-quinuclidinyl)benzamides and thiobenzamides, namely 2-alkoxy-N-(1-azabicyclo[2.2.2]oct-3-yl)-benzamides and thiobenzamides which have been observed to exhibit antischizophrenic properties in warm blooded animals.

BACKGROUND OF THE INVENTION

Quinuclidine analogues of sulpiride were prepared and studied by Mikhlina, E. E. et al as reported in *Khim-Farmatsevt. Zh.* 10, No. 11, 56–60 (1976); C.A. 86: 155489r exemplified by the compound: 5-aminosulphonyl-N-(1-azabicyclo[2.2.2]oct-b 3-yl)-2-methoxybenzamide. This compound and others in the series were reported by the authors not to have antiemetic activity. The above named compound was reported in USSR Patent SU-414-261 to have neuroleptic activity. In comparison, the compounds of the present invention show strong gastrokinetic and antiemetic activity without neuroleptic activity (blockade of d-amphetamine lethality in mice).

Syntheses of 4-amino-N-(1-azabicyclo[2.2.2]oct-3-yl)benzamide and N-(1-azabicyclo[2.2.2]oct-3-yl)benzamide were reported by Mikhlina, E. E. et al in *Khim-Farmatsevt. Zh.* 7, 20–24 (1974); C.A. 79, 146358a and the latter in *Khim. Geterosikl. Soedin., Akad. Nauk. Latv. SSR* 243-9 (1966); C.A. 65: 2220b. These compounds were reported to exhibit hypotensive, narcotic and ganglionic stimulation and blocking activities, properties not seen in the compounds of the present invention.

Synthesis of 4-amino-N-(1-azabicyclo[2.2.2]oct-3-yl)-3-chloro-5-trifluoromethylbenzamide was reported in DE-A-2,548,968; C.A. 87, 68001c and in equivalently related U.S. Pat. No. 4,093,734 from 4-amino-3-chloro-5-trifluoromethyl benzoic acid chloride and 3-aminoquinuclidine. The compound is in a class among pyrrolidinyl and piperidinyl benzamides which are said to be useful as anxiolytics, anticonvulsives, antiemetics and antiulcerogenics. None of the compounds have orthoalkoxy substitution on benzamide as do the compounds of the present invention.

It is widely recognized that substituted benzamides are a class of drugs known to be effective in psychiatry and gastroenterology (Sulpiride and other Benzamides; International Workshop on Sulpiride and other benzamides, Florence, Feb. 17–18 (1978), Raven Press]. However, the 2-alkoxy-N-(1-azabicyclo[2.2.2]oct-3-yl)benzamides used in this invention have now been found to have marked anxiolytic properties.

EP-A-0158532 and FR-A-2529548 disclose the compounds useful in the present invention, but are concerned with activity on the gastrointestinal tract.

Figure 1:
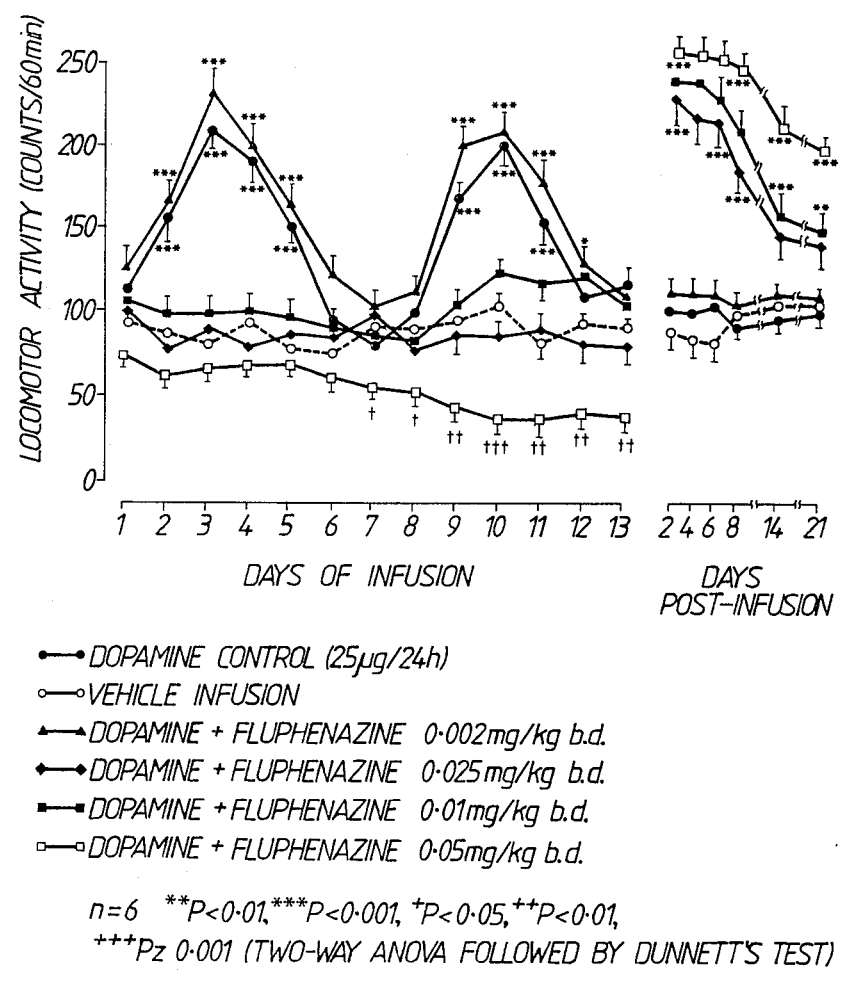
FIG. 1. depicts a graph showing the antagonism by fluphenazine of the hyperactivity caused by dopamine infused bilaterally into the rat nucleus accumbens.

●—● dopamine control (25 μg/24 h). ○—○ vehicle infusion.

▲—▲ dopamine+fluphenazine 0.02 mg/kg b.d.,
◆—◆ dopamine+fluphenazine 0.025 mg/kg b.d.,
■—■ dopamine+fluphenazine 0.01 mg/kg b.d.,
□—□ dopamine+fluphenazine 0.05 mg/kg b.d. n=6.
$P<0.01$, *$P<0.001$, +$P<0.05$, ++$P<0.01$, +++$P<0.001$ (two-way ANOVA followed by Dunnett's test).

FIGS. 2A–2C. depicts graphs showing the ability of Compound 1 to antagonise a raised mesolimbic dopamine hyperactivity. Data is given for Compound 1 at 0.0001 and 0.001 mg/kg b.d. n=6. *$P<0.01$–$P<0.001$ (dopamine hyperactivity), +$P<0.001$ (antagonism dopamine hyperactivity).

FIGS. 3A–3C. depicts graphs showing the ability of Compound 1 to antagonise a raised mesolimbic dopamine hyperactivity. Data is given for Compound 1 at 0.01, 0.1 and 1 mg/kg b.d. n=6. *$P<0.05$–$P<0.001$ (dopamine hyperactivity). Suppression of the second peak of hyperactivity by Compound 1 at 0.01 mg/kg b.d. was significant to $P<0.001$. As in FIG. 2, data is given for 13 days of infusion and 8 days post-infusion.

DESCRIPTION OF PREFERRED EMBODIMENTS

2-Alkoxy-N-(1-azabicyclo[2.2.2]oct-3-yl)benzamides and thiobenzamides used in this invention have the formula:

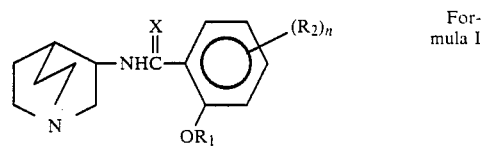

Formula I wherein X represents oxygen or sulphur, $R_1$ represents loweralkyl and $R_2$ represents hydrogen, halo, 4,5-benzo, alkoxy or Am wherein Am represents amino, methylamino or dimethylamino, and n is 1 or 2, and the pharmaceutically acceptable acid addition salts thereof.

In the further definition of symbols in the formulae hereof and where they appear elsewhere throughout this specification and the claims, the terms have the following significance.

The term "loweralkyl" as used herein includes straight and branched chain radicals of up to eight carbons inclusive and is exemplified by such groups as methyl, ethyl, propyl, isopropyl, butyl, amyl, hexyl, heptyl, and octyl radicals and the like. The term "loweralkyl" has the formula —O—loweralkyl.

The terms "halo" or "halogen" when referred to herein include fluorine, chlorine, bromine and iodine unless otherwise stated.

"Pharmaceutically acceptable acid addition salts" include the acid addition salts, hydrates, alcoholates and salts of the compounds, which salts are pysiologically compatible in warm blooded animals. The acid addition salts may be formed by either strong or weak acids. Representative of strong acids are hydrochloric, sulphuric and phosphoric acids. Representative of weak acids are fumaric, maleic, succinic, oxalic, citric, tartaric, cyclohexamic and the like.

Protected amino groups used in synthesis are acetylamino or benzoylamino radicals and the like on the benzamide moiety mentioned hereinbelow in synthetic methods.

The symptoms of schizophrenia have been associated, at least in part, with a raised mesolimbic dopamine function. This can be mimicked experimentally by infusing dopamine slowly and persistently into a mesolimbic area. In the present studies dopamine was infused slowly and persistently into the nucleus accumbens of rat brain. This causes a hyperactivity which is neuroleptic sensitive. The dopamine infusion response is sensitive to antagonism by the above compounds which indicates an antischizophrenic potential for them.

The antischizophrenic activity was determined by the method of Costall and Naylor, details of which are to be found in the pharmacology examples later in this specification. In brief, the method involves assessing the antagonism of hyperactivity of rats caused by dopamine infusion.

It is therefore a primary object to provide a use for 2-alkoxy-N-(1-azabicyclo[2.2.2]oct-3-yl-benzamides and thiobenzamides.

A further object is to provide 2-alkoxy-N-(1-azabicyclo[2.2.2]oct-3-yl-benzamides and thiobenzamides having antischizophrenic properties.

A still further object is to provide means for controlling schizophrenia.

Preparations of Benzamides

The benzamido compounds of Formula I are prepared by reacting a suitably activated benzoic acid derivative with 3-aminoquinuclidine to form the corresponding benzamide under a variety of conditions. Two general methods, A and B, are illustrated in the following equations:

Method A, using an Acid Chloride

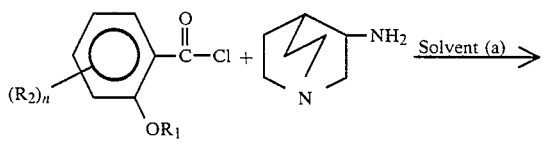

$R_1$, $R_2$ and n are as defined under
Formula I except $R_2$ cannot be
unprotected amino.
(a) Suitable solvents are chloroform
and diethyl ether.
Method A is illustrated by Examples 5, 6, 7 and 9.

Method B, using 1,1'-Carbonyldiimidazole

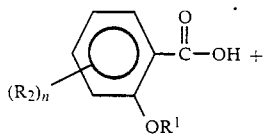

-continued

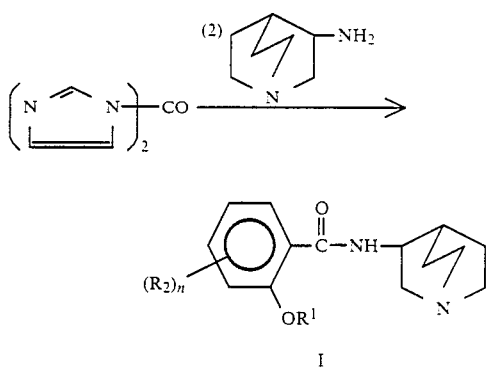

$R_1$, $R_2$ and n are as defined under Formula I.
(a) e.g., tetrahydrofuran.
Method B is illustrated in Examples 1, 3 and 8.

Compounds wherein $R_2$ is primary amino may also be prepared from a compound prepared by Methods A or B, wherein $R_2$ is nitro by catalytic reduction of the nitro compound.

Alternatively, compounds wherein $R_2$ is amino may be prepared by procedures of Method A utilizing a starting benzoyl halide wherein the amino group has been protected, or they may be prepared from compounds prepared in Method A or B wherein $R_2$ is nitro and reducing the nitro radical to an amino radical.

Preferably, the compounds wherein $R_2$ is amino or methylamino are prepared by Method B.

The free base of any compound of Formula I from its acid addition salt may be regenerated by usual procedures of partitioning between dilute aqueous base and a suitable solvent, separating the solvent layer, drying and evaporating.

Preparation of Thiobenzamides

The preparation of the thiobenzamido compounds of Formula II may be accomplished by mixing and reacting a benzamido compound of Formula I with a mixture of phosphorus pentasulphide ($P_2S_5$) and potassium sulphide ($K_2S$) or by mixing and reacting 3-aminoquinuclidine with an appropriately substituted benzaldehyde and sulphur. The reaction sequences are illustrated by the following:

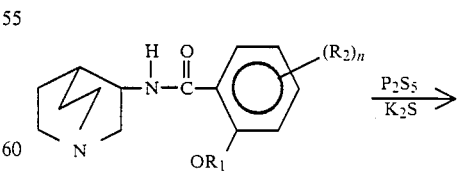

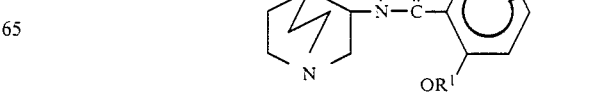

-continued

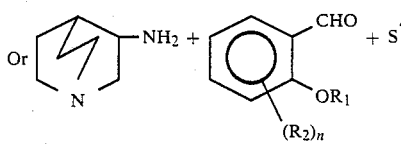

In these methods, compounds wherein $R_2$ is nitro may be reduced to compounds wherein $R_2$ is amino.

A preferred group of compounds encompassed by Formula I have the formula:

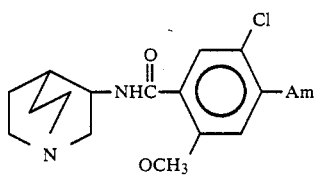                    $I_c$ wherein Am is amino (i.e., —$NH_2$) or methylamino. The compounds are highly potent as gastric emptiers and as anti-emetics in conjunction with cisplatin cancer treatment, being more potent than metoclopramide and devoid of undesirable neuroleptic side effects even at much higher doses than required for their gastric emptying and antiemetic effects. As will be recognized from the above description, these compounds (Ic) are preferably prepared by Method B.

The following examples are provided merely by way of illustrating the methods of preparation and compounds and are not to be construed as being limiting in nature.

EXAMPLE 1

4-Amino-N-(1-azabicyclo[2.2.2]oct-3-yl)-5-chloro-2-methoxybenzamide, fumarate [1:1]

In a closed system equipped with an oil bubbler, 30 ml of tetrahydrofuran was added to a mixture of 4-amino-5-chloro-2-methoxybenzoic acid, 2.02 g, (0.010 mole) and 1,1'-carbonyldiimidazole, 1.62 g (0.010 mole) with stirring. When evolution of carbon dioxide ceased, nitrogen was bubbled through the reaction mixture for 1 hr. A solution of 3-aminoquinuclidine, 1.26 g, (0.010 mole) in 10 ml tetrahydrofuran was added dropwise to the stirred reaction mixture and stirring at room temperature continued for 3 hrs. TLC analysis (3% conc. ammonium hydroxide solution in methanol) showed some product formation. The mixture was heated at reflux temperature for 18 hours and then concentraded to an oil. TLC analysis showed the presence of the product, imidazole, and 3-aminoquinuclidine. The oil was dissolved in methylene chloride (75 ml) and washed twice with 50 ml portions of aqueous sodium bicarbonate solution. The methylene chloride layer was dried over anhydrous magnesium sulphate and concentrated to yield 2.0 g (67%) of a glassy amorphous solid, the free base of the title compound.

In another reaction on a 0.020 mole scale, 5.18 g (83.8%) of the product as the free base was obtained.

The products were combined, dissolved in methanol (20 ml) and the solution and treated with a solution of fumaric acid (2.73 g) in methanol (50 ml). Absolute ether was added to precipitate the salt which was collected by filtration and recrystallized from methanol-water (200:20) with isopropyl ether added to the point of incipient cloudiness. The recrystallized salt (5.38 g) melted at 223°–225° C.

Analysis: Calculated for $C_{19}H_{24}N_3O_6Cl$: C, 53.59; H, 5.68; N, 9.89. Found: C, 53.35; H, 5.72; N, 9.95.

EXAMPLE 2

4-Amino-N-(1-azabicyclo[2.2.2]oct-3-yl)-5-chloro-2-methoxybenzamide, hydrochloride, hydrate (1:1:1)

To an isopropyl alcohol solution of the free base of the title compound such as was obtained by the procedure of Example 1 is added an equal molar amount of 37% (conc.) hydrochloric acid. The crude salt is separated by filtration and recrystallized from acetone-water to give the title compound, m.p. 158°–160° C.

EXAMPLE 3

N-(1-Azabicyclo[2.2.2]oct-3-yl)-5-chloro-2-methoxy-4-methylaminobenzamide, fumarate [1:1]

To a mixture of 1,1'-carbonyldiimidazole, 1.23 g (0.00756 mole) and 5-chloro-2-methoxy-4-methylaminobenzoic acid, 1.63 g (0.00756 mole) was added 50 ml of tetrahydrofuran. Nitrogen was bubbled into the solution for 30 minutes to remove any carbon dioxide that was present. To the solution was added 3-aminoquinuclidine, 0.95 g, (0.00756 mole) in one portion, and the reaction mixture was stirred at ambient temperature for 16 hours. The reaction mixture was concentrated to an oil which was shown to be 1:1 mixture of the free base of the product and imidazole. The mixture was dissolved in 20 ml methanol and treated with a solution containing 0.47 g fumaric acid in 20 ml of hot methanol. Upon cooling, 1.52 g of white solid formed. Recrystallization from water-methanol gave 0.84 g of the product as a white solid; m.p. 237°–238° C.

Analysis: Calculated for $C_{20}H_{26}N_3O_6Cl$: C, 54.61; H, 5.96; N, 9.55. Found: C, 54.61; H, 5.98; N, 9.51.

EXAMPLE 4

N-(1-Azabicyclo[2.2.2]oct-3-yl)-5-chloro-2-methoxy-4-(methylamino)-benzamide, hydrochloride (1:1)

To an isopropyl alcohol solution of the free base of the title compound, such as was obtained by the procedure of Example 3, is added an equal molar amount of 37% (conc.) hydrochloric acid. The crude salt is separated by filtration and recrystallized from ethanol-water to give the title compound, m.p. 255°–258° C.

EXAMPLE 5

N-(1-Azabicyclo[2.2.2]oct-3-yl)-2-methoxybenzamide, fumarate [1:1]hemihydrate

In a closed system equipped with an oil bubbler, a solution of 2-methoxybenzoyl chloride, 2.76 g (0.0016 mole) in 50 ml absolute ether was added dropwise over 10 min to a stirred solution of 3-aminoquinuclidine, 1.81 g (0.0144 mole) in 100 ml absolute ether. After the addition was completed, the mixture was stirred at room temperature for an additional 2 hrs. The solid hydrochloride salt was collected by filtration under nitrogen. The salt (3.83 g) was dissolved in sodium bicarbonate solution and extracted twice with 25 ml portions of methylene chloride. The extract was dried over magnesium sulphate and concentrated to yield 1.25 g clear oil (33.3%). TLC analysis (3% conc. ammonium hydroxide in methanol) showed the free base to be pure. A solution of 1.17 g of the free base in 5 ml methanol was treated with a solution of 0.52 g fumaric acid in 10 ml methanol. Isopropyl ether was added to give approximately 100 ml of solution from which the fumarate salt precipitated. The salt was collected under nitrogen and dried in a vacuum oven at 60° C. overnight. NMR and elemental analyses showed that the product was a hemihydrate.

Analysis: Calculated for $C_{19}H_{25}N_2O_{6.5}$: C, 59.21; H, 6.54; N, 7.27. Found: C, 59.18; H, 6.30; N, 7.25.

EXAMPLE 6

N-(1-Azabicyclo[2.2.2]oct-3-yl)-2,4-dimethoxybenzamide hydrochloride [1:1]

A mixture of 3-aminoquinuclidine dihydrochloride, 6.95 g, (0.0349), 2,4-dimethoxybenzoyl chloride, 700 g, (0.0349 mole), anhydrous sodium carbonate, 36.99 g, (0.349 mole), 175 ml water, and 175 ml chloroform was stirred rapidly to achieve good mixing of the 2 layers for 20 hrs. The chloroform layer was then separated, washed with water, dried over anhydrous magnesium sulphate, and concentrated to an impure oil. The oil was triturated twice with 20 ml portions of petroleum ether to remove some impurities. The oil was then dissolved in ether and filtered to remove a small amount of insoluble material. The filtrate was treated with ethereal hydrogen chloride and the resulting salt collected to yield 2.70 g (23.7% yield) white solid. The salt was recrystalized from ethanol-isopropyl ether. Further recrystallization from methanol-ethyl ether yielded a white solid, m.p. 211°–212° C. The NMR analysis was satisfactory.

Analysis: Calculated for $C_{16}H_{23}N_2O_3Cl$: C, 58.80; H, 7.09; N, 8.57. Found: C, 58.38; H, 7.13; N, 8.44.

EXAMPLE 7

N-(1-Azabicyclo[2.2.2]oct-3-yl)-2,4-dimethoxybenzamide, sulphate [1:1]

In a closed system equipped with an oil bubbler, a solution of 2,4-dimethoxybenzoyl chloride, 13.08 g, (0.0652 mole) in 200 ml absolute ether was dded dropwise over 30 minutes to a stirred solution of 3-aminoquinuclidine, 7.80 g, (0.0619 mole) in 200 ml absolute ether. The mixture was stirred overnight, and the solid hydrochloride salt of the product was filtered under nitrogen. The material was dried in a vacuum oven at 40° C. to give 18.70 g (92%). A 2.94 g (0.009 mole) portion of the hydrochloride salt in 20 ml methanol was treated with a solution of sodium methoxide prepared from 0.23 g (0.010 mole) sodium metal and 10 ml methanol. After standing a few minutes, the mixture was filtered and the filtrate concentrated on a rotary evaporator, and the residue was triturated with 75 ml methylene chloride. After filtering to remove some insuluble solids, the filtrate was concentrated to yield 2.53 g of the free base of the title compound (97% recovery from the hydrochloride salt). The free base was dissolved in 100 ml acetone and concentrated sulphuric acid (0.483 ml) added dropwise with stirring. The solid that formed was collected under nitrogen to give 2.76 g of the salt which recrystallized from methanol-isopropyl ether and dried in a vacuum oven at 60° C. for 2 hrs and then overnight at 78° C.; m.p. 223°–225° C.

Analysis: Calculated for $C_{16}H_{24}N_2O_7S$: C, 49.47; H, 6.23; N, 7.23. Found: C, 49.41; H, 6.30; N, 7.25.

EXAMPLE 8

N-(1-Azabicyclo[2.2.2]oct-3-yl)-2,4-dimethoxybenzamide, fumarate [1:1.5]

In a closed system equipped with an oil bubbler, tetrahydrofuran, 100 ml, was added to a mixture of 2,4-dimethoxybenzoic acid, 3.64 g (0.020 mole) and 1,1′carbonyldimidazole, 3.24 g (0.020 mole). No evolution of carbon dioxide was observed and after stirring for 3 hrs, TLC (ethyl acetate) and mass spectral analysis showed that the starting material had reacted to form (2,4-dimethoxybenzoyl)imidazole and imidazole. A solution of 3-aminoquinuclidine, 2.52 g (0.020 mole) in 10 ml tetrahydrofuran was added to the mixture, and the solution was heated to reflux temperature for 1 hr and then allowed to stand overnight at room temperature. A solution of fumaric acid, 2.32 g (0.020 mole in 50 ml methanol was added to the reaction mixture. Tetrahydrofuran was added until the solution became slightly turbid. The solution was chilled in a refrigerator. The solid which precipitated from solution was collected by filtration and found to be a fumarate salt of 3-aminoquinuclidine. The filtrate was concentrated to an oil and triturated with tetrahydrofuran. The solid precipitate which formed on standing was filtered and shown by TLC (3% concentrated ammonium hydroxide in methanol) to be the desired product plus traces of imidazole and 3-aminoquinuclidine. Recrystallization from methanol-iropropyl ether gave 5.41 g white crystalline solid (67% yield calculated as the monofumarate). NMR and elemental analysis showed the salt to contain less than one equivalent of fumaric acid. The salt was dissolved in boiling methanol (50 ml) and treated with an additional 0.77 g (0.0066 mole) fumaric acid in 10 ml hot methanol. Isopropyl ether was added until the hot solution became turbid. The solid obtained on cooling was collected, recrystallized from methanol-isopropyl ether and dried in a vacuum oven at 78° C. overnight. NMR and elemental analysis showed the salt to be a 1.5 fumarate, m.p. 192°–192.5° C.

Analysis: Calculated for $C_{22}H_{28}N_2O_9$: C, 56.89; H, 6.08; N, 6.03. Found: C, 56.81; H, 6.13; N, 6.04.

EXAMPLE 9

N-(1-Azabicyclo[2.2.2]oct-3-yl)-2-propoxybenzamide hydrochloride [1:1]

To a solution of 3.82 g (0.0192 mole) of 3-amino quinuclidine dihydrochloride in about 25 ml of carbon dioxide-free water was added 8 g (0.025 mole) of barium hydroxide octahydrate. The mixture was warmed for 5 minutes and then dried to a powder on a rotary evaporator. While protecting from contamination with carbon dioxide in the atmosphere, the powder was extracted in sequence with hot benzene and a 1:1 mixture of benzene-methylene chloride solution. The combined extracts were dried over magnesium sulphate and the mixture filtered. To the filtrate with agitation was added dropwise a solution of 3.4 g (0.0171 mole) of 2-propoxybenzoyl chloride in 50 ml of methylene chloride. The mixture was warmed on a steam bath to evaporate about 75% of the methylene chloride. Ligroin (60-110) was added and the mixture solidified. The solid was recrystallized from anhydrous ethyl alcohol to give 3.9 g (62.0%), m.p. 210°–211° C.

Analysis: Calculated for $C_{17}H_{25}N_2O_2Cl$: C, 62.86; H, 7.75; N, 8.62. Found: C, 62.62; H, 7.59; N, 8.54.

EXAMPLE 10

N-(1-Azabicyclo[2.2.2]oct-3-yl)-3-methoxy-2-naphthalenecarboxamide, hydrochloride [1:1]

A solution of 1.69 g (0.00768 mole) of 3-methoxy-2-naphthoic acid chloride in 15 ml of methylene chloride was added dropwise to a stirred solution of 0.97 g (0.00768 mole) of 3-aminoquinuclidine in 25 ml of methylene chloride in a closed system equipped with an oil bubbler. The reaction mixture was stirred overnight at ambient temperature, and then concentrated to give an off-white glassy solid. Two recrystallizations from methanol-isopropyl ether gave 1.95 g (73.4%) of the product as an off-white solid which was vacuum dried at ambient temperature, m.p. 248°–252° C.

Analysis: Calculated for $C_{19}H_{23}N_2O_2Cl$: C, 65.79; H, 6.68; N, 8.08. Found: C, 65.40; H, 6.72; N, 8.01.

EXAMPLE 11

4-Amino-N-(1-azabicyclo[2.2.2]oct-3-yl)-5-chloro-2-methoxythiobenzamide fumarate One half mole of 4-amino-N-(1-azabicyclo[2.2.2]oct-3-yl)-5-chloro-2-methoxybenzamide fumarate is partitioned between dilute sodium hydroxide and 400 ml of benzene. The benzene solution is dried with sodium sulphate and distilled to a volume of 250 ml. To this is added a finely-ground mixture of 9 g of phosphorous pentasulphide and 9 g of potassium sulphide. The mixture is refluxed for 4 hr. and an additional 9 g of phosphorous pentasulphide is added and reflux continued for 2 hr. The benzene is decanted off. The solid is dissolved in a suitable solvent and reacted with fumaric acid to give the title compound.

Pharmaceutical Methods and Compositions

Generally, the method of controlling schizophrenia in accordance with this invention comprises administering internally to warm blooded animals including human beings certain 2-alkoxy-N-(1-azabicyclo[2.2.2]oct-3-yl)benzamides and thiobenzamides of Formula I, preferably Formula Ic, or a non-toxic organic or inorganic acid addition salt thereof in a wide variety of pharmaceutical forms well known in the art, preferably with a non-toxic pharmaceutical carrier such as is described below in an amount to control schizophrenia.

The active agent is administered orally, subcutaneously, intravenously or intramuscularly or parenterally and, if necessary, in repeated doses until satisfactory response is obtained. Daily dosage regimes of the active agent will generally be such as to attain the dosages given below. The compounds may thus be presented in a therapeutic composition suitable for oral, parenteral, subcutaneous, intramuscular, intraperitoneal or intravenous administration. Thus, for example, compositions for oral administration can take the form of elixirs, capsules, tablets or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid; e.g. water or arachis oil contained in ampoules.

The pharmaceutical compositions may be formulated to contain from about 5 ng/kg to about 10 mcg/kg body weight, preferably 1 mcg/kg body weight or less. It will generally be the case that the dose will be less than 0.2–2.0 mg/kg per day as a loss of selectivity of action may result. It is necessary that the active ingredient of Formula I constitute an effective amount.

In all of the above, it is only necessary that a suitable effective dosage will be consistent with the dosage form employed. The exact individual dosages, as well as daily dosages, will of course be determined according to standard medical principles under the direction of a physician or veterinarian.

PHARMACOLOGICAL EXAMPLE

Figure 2:
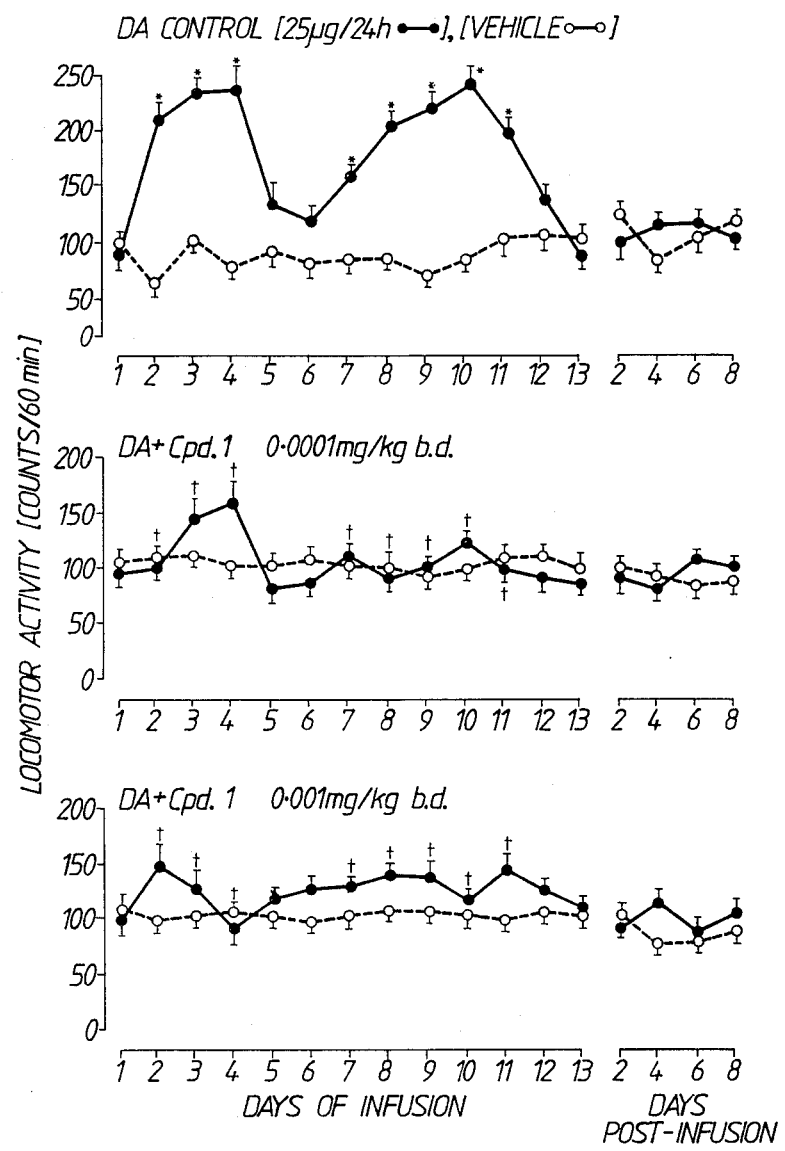
Figure 3:
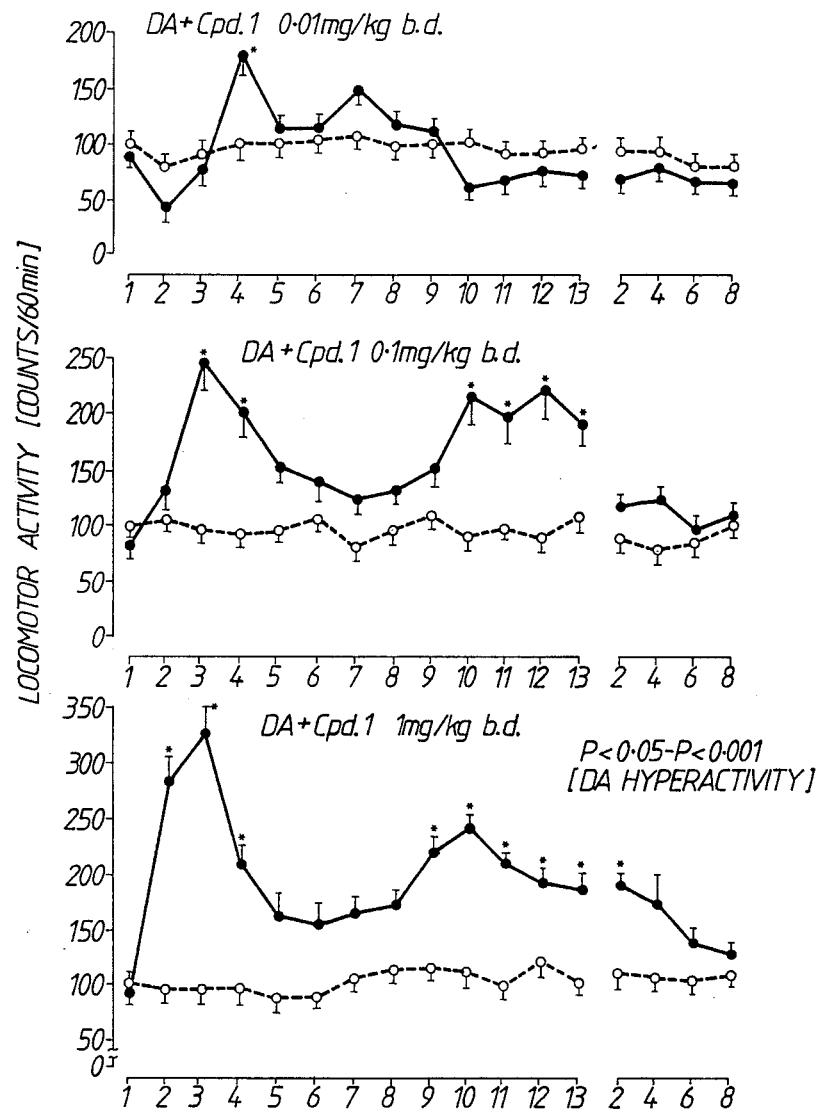

This example refers to the accompanying drawings, in which:

FIG. 1 shows antagonism by fluphenazine of hyperactivity caused by dopamine infused bilaterally into the rat nucleus accumbens;

FIG. 2 shows the ability of the compound of Example 1 to antagonise a raised mesolimbic dopamine activity; and FIG. 3 shows the ability of the compound of Example 1 to antagonise a raised mesolimbic dopamine hyperactivity.

Rat Studies

Male Sprague-Dawley (CD, Bradford strain) rats were used, weighing 300±25 g at the time of initial stereotaxic surgery.

The behavioural measure throughout was hyperactivity assessed in individual photocell cages constructed of perspex, 25×15×15 cm high, each fitted with one photocell unit placed off-centre. The cages were screened. Interruptions of the light beams were continuously monitored and the level of locomotor activity expressed in counts/5 min.

Rats were subject to standard stereotaxic techniques for the implantation of chronically indwelling guide cannulae for subsequent bilateral intracerebral infusion into the centre of the nucleus accumbens (Ant. 9.4, Vert. 0.0, Lat. ±1.6, atlas of De Groot). Rats were anaesthetised with chloral hydrate (300 mg/kg s.c.) and placed in a Kopf stereotaxic instrument. Implanted guides were constructed of stainless steel, 0.65 mm diameter, held bilaterally in perspex holders. Guides terminated 3.5 mm above the centre of the nucleus accumbens and were kept patent for a 14-day recovery period using stainless steel stylets extending 0.5 mm beyond the guide tips.

After the 14 days recovery rats were anaesthetised with halothane/$N_{20}$, $O_2$ for the s.c. implantation in the back neck region of two Alzet osmotic minipumps each attached via polythene tubing, running subcutaneously, to stainless steel injection units (0.3 mm diameter) which were made to fit permanently into the previously implanted guides in place of the stylets, but terminating 3.5 mm below the guide tips at the centre of the nucleus accumbens. The pumps had previously been filled with dopamine solution (2.17 mcg/mcl, dopamine hydrochloride, Koch Light, prepared in $N_2$ bubbled solution containing 0.1% sodium metabisulphite), or its solvent, and the entire injection unit primed for between 5 and 8 hr at 37° C. The pumps delivered dopamine or its solvent at a constant rate of 0.48 mcl/hr from the time of implantation, and thus provided an intra-accumbens dose of dopamine of 25 mcg over a 24 hr period. Pumps were removed on day 13. Rat spontaneous locomotion was measured between 8.00 and 11.00 am. The compound of Example 1 ("Compound 1") and fluphenazine were given twice daily at 7.30 am and 7.30 pm.

RESULTS

The hyperactivity caused by dopamine infusion into the nucleus accumbens of rat was antagonised by the classical neuroleptic agent fluphenazine at doses of 0.025–0.05 mg/kg given twice daily. At the highest dose of 0.05 mg/kg the fluphenazine treatment not only suppressed the dopamine response but caused clear motor depression to values below control (FIG. 1). After 13 days of treatment, both the dopamine infusion and the fluphenazine treatment were stopped, and in those rats where the fluphenazine had successfully suppressed the dopamine hyperactivity a marked rebound hyperactivity developed which persisted in excess of 21 days (FIG. 1).

Similarly to fluphenazine, treatment with Compound 1 was shown to inhibit the hyperactivity caused by dopamine infused into the rat nucleus accumbens. However, Compound 1 was considerably more potent than fluphenazine and complete antagonism of the dopamine response was achieved at 0.0001 mg/kg b.d. In contrast to fluphenazine, treatment with Compound 1, whilst 'controlling' the dopamine hyperactivity, was never seen to cause undue motor depression. Further, there was no rebound hyperactivity on abrupt withdrawal of treatment (FIGS. 2 and 3). If the dose of compound was increased considerably to 0.1–1.0 mg/kg b.d. there was a loss of selectivity of action and hyperactivity developed during the period of dopamine infusion (FIG. 3).

It is thus clear that compounds of the invention have a clear potential to antagonise the behavioural consequences of a raised mesolimbic dopamine function, and that this can be achieved without sedation or depression of locomotor activity to values below normal responding, and without problems on drug withdrawal. The test system described is very selective for the detection of agents having clinical anti-schizophrenic activity.

Thus low doses of compounds of the invention are shown to control the behavioural consequences of a mesolimbic dopamine excess. This activity can be achieved without undue motor depression and without problems on cessation of drug treatment. Whilst the control of the hyperactivity caused by a mesolimbic dopamine excess can also be achieved using a classical neuroleptic agent such as fluphenazine, the action of fluphenazine can lead to locomotor depression and a marked rebound hyperactivity on withdrawal of therapy. It should be noted that the effective therapy is achieved using low doses of compounds of the invention: a loss of selectivity of action occurs as the doses are increased some 1,000–10,000 fold above the lowest effective dose.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

We claim:

1. A method of treating schizophrenia in a warm-blooded animal comprising administering to said animal a pharmaceutical composition comprising a compound of general formula I:

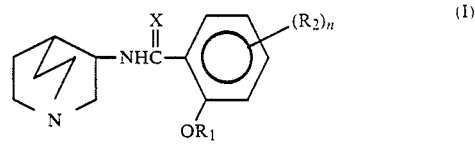

wherein:
X represents oxygen or sulphur;
R$^1$ represents loweralkyl;
R$^2$ represents hydrogen, halo, 4,5-benzo, loweralkoxy, amino, methylamino or dimethylamino; and
n is 1 or 2;
or a pharmaceutically acceptable acid addition salt thereof, in an amount sufficient to control schizophrenia; and a pharmaceutically acceptable carrier.

2. The method of claim 1, wherein R$^2$ is a 3-halo substituent.

3. The method of claim 1 or 2, wherein R$^2$ is a 4-amino, 4-methylamino or 4-dimethylamino substituent.

4. The method of claim 1 or 2, wherein X is oxygen.

5. The method of claim 3, wherein X is oxygen.

6. A method of treating schizophrenia in a warm-blooded animal comprising administering to said animal a pharmaceutical composition comprising a compound selected from the group consisting of
4-amino-N-(1-azabicyclo[2.2.2]oct-3-yl)-5-chloro-2-methoxybenzamide,
N-(1-azabicyclo[2.2.2]oct-3-yl)-5-chloro-2-methoxy-4-methylaminobenzamide,
N-(1-azabicyclo[2.2.2]oct-3-yl)-2-methoxybenzamide,
N-(1-azabicyclo[2.2.2]oct-3-yl)-2,4-dimethoxybenzamide,
N-(1-azabicyclo[2.2.2]oct-3-yl)-2-propoxybenzamide,
4-amino-N-(1-azabicyclo[2.2.2]oct-3-yl)-5-chloro-2-methoxybenzamide,
N-(1-azabicyclo[2.2.2]oct-3-yl)-5-chloro-2-methoxy-4-methylaminobenzamide, and
N-(1-azabicyclo[2.2.2]oct-3-yl)-3-methoxy-2-naphthalenecarboximide,
or a pharmaceutically acceptable salt thereof, in an amount sufficient to control schizophrenia; and a pharmaceutically acceptable carrier.

7. The method of claim 1 or 6, wherein said compound is administered at a dosage of 5 ng/kg body weight to 10 mcg/kg body weight of said warm-blooded animal.

8. The method of claim 7, wherein said warm-blooded animal is a human.

* * * * *